(12) United States Patent
Rodgers

(10) Patent No.: US 7,777,631 B2
(45) Date of Patent: Aug. 17, 2010

(54) BODY CHIP

(76) Inventor: James Neil Rodgers, 8853 214th Place, Langley, BC (CA) V1M 2H9

( * ) Notice: Subject to any disclaimer, the term of this patent is extended or adjusted under 35 U.S.C. 154(b) by 448 days.

(21) Appl. No.: 11/741,760

(22) Filed: Apr. 29, 2007

(65) Prior Publication Data

US 2008/0266107 A1    Oct. 30, 2008

(51) Int. Cl.
*G08B 13/14* (2006.01)

(52) U.S. Cl. .............. 340/572.8; 340/572.1; 340/573.1; 340/573.3; 340/500; 600/407

(58) Field of Classification Search .............. 340/500, 340/572.8, 573.3, 540, 573.1; 424/9.1, 401; 428/402; 600/407, 411, 420, 421, 423, 373, 600/377; 623/23.57; 235/435; 604/19, 31, 604/48, 93.01, 174, 175
See application file for complete search history.

(56) References Cited

U.S. PATENT DOCUMENTS

| 6,497,729 | B1 * | 12/2002 | Moussy et al. | ............ 623/23.57 |
| 2005/0063906 | A1 * | 3/2005 | Kraizer et al. | ................ 424/9.1 |
| 2006/0289640 | A1 * | 12/2006 | Mercure et al. | ............. 235/435 |
| 2007/0063852 | A1 * | 3/2007 | Brungot et al. | ........... 340/573.3 |
| 2007/0123772 | A1 * | 5/2007 | Euliano et al. | ............... 600/407 |
| 2009/0028910 | A1 * | 1/2009 | DeSimone et al. | ........... 424/401 |
| 2009/0220789 | A1 * | 9/2009 | Desimone et al. | ........... 428/402 |

OTHER PUBLICATIONS

Lawrence D. Maloney, Feb. 7, 2005, Chip on Your Arm, An RF device to be implanted in the triceps of a user makes medical records portable, all 5 pages.*

* cited by examiner

*Primary Examiner*—George A Bugg
*Assistant Examiner*—Sisay Yacob
(74) *Attorney, Agent, or Firm*—James Neil Rodgers

(57) ABSTRACT

This Invention contemplates a system and method to manufacture an active RFID integrated circuit as a system on a chip which is powered by enzymes located in mammalian bodies. According to this Invention the active integrated circuit system on a chip is manufactured of a glass capsule containing a porous membrane which allows the free flow of bodily fluids into and out of the capsule. The enzymes in the bodily fluids of mammals produce sufficient electrical charge to power an active RFID transponder. This electrical charge is harnessed through the auspices of a standard chemical process utilizing a nano anode and cathode manufactured as an integral part of the system on a chip integrated chip capsule. The capsule or casing is coated with bio friendly enzymes which promote the surrounding tissue to grow up to the glass casing or capsule and bond with it. This is for the purpose of securing the capsule in one position in the body. The result is an active RFID transponder mammalian implant which can be interrogated from distances greater than those available with passive transponders. The negative fluidic and tissue influence of the mammalian body on electro magnetic signals is obviated by low frequency interrogation. The antenna of the system on a chip bodily implant is tuned to a specific frequency so that specific bodily fluids or tissue at the position of the body where the implant is positioned will not cause detuning of the antenna.

4 Claims, No Drawings

BODY CHIP

Radio Frequency Identification (herein "RFID") has been an appropriate and successful technology in the field of supply chain management. Persons ordinarily skilled in the art of RFID are well aware of this success. However, RFID has not proven viable in the medical field or in the human or animal body tracking field. The problem is that the fluids and tissue in the mammalian body detune the RFID system. This Invention contemplates a method and a system whereby the chemicals in the body power an RFID transponder. This novel and inventive step transforms the transponder located within a human or animal body from a passive chip into an active chip. This non-obvious step allows any RFID system to overcome the detuning effects of bodily fluids. The Inventor refers to this Invention as the "Body Chip". Currently the trade name "Body Chip" is the subject of a U.S. Trade Name application by the Inventor. This Invention incorporates by reference Rodgers Application 11676304 titled "RFID interrogation of liquid/metal" and Rodgers Application 11683056 titled "RFID silicon antenna" and Rodgers Application 11686946 titled "Precisely tuned RFID antenna".

BACKGROUND OF THE INVENTION

RFID is a system in which radio frequency communication is used to exchange data. Usually this is accomplished between mobile devices equipped with a memory component hooked to a host computing system. RFID systems are classified in accordance with the frequency used to excite the memory unit. They can also be classified by the type of carrier wave modulation used to interrogate the RFID tag and the method of data encoding. Many characteristics of an RFID system are determined by the excitation frequency. This includes the read/write range between the reader and tag, noise immunity, and penetration through various non-metallic objects. The excitation frequency has a bearing on antenna type, size and shape.

The frequencies which are commercially available can be broken into three bands. First there is the low frequency band which operates between 100 and 300 kHz. Second the medium frequency which operates between 10 and 15 MHz. Third there is the high frequency systems which can be found at 850 to 950 MHz and at 2.4 to 5.8 GHz. There are a number of key components of an RFID system. The remote portion of the system is referred to as a tag or transponder. It contains an antenna, an integrated circuit, data storage space and can have the ability to be rewritable. In a passive set up the reader or interrogator provides power to the tag. A host computer interfaces with the reader and directs the interrogation via parallel, serial or bus communications.

The first function of the system is the initiating reader circuit which is based on a transfer of energy between two resonant circuits. The tag responds and is comprised of a coil or etched antenna and an application specific integrated circuit. The tags can be manufactured with or without internal power. Those tags without power are called passive. They are powered by charging an internal capacitor using the onboard antenna in conjunction with an externally provided electromagnetic field. Passive tags last for a long period of time and require no additional maintenance cost. In contrast, active tags are manufactured with onboard batteries to power the electronics and typically allow longer ranges between the host computer and tag via signal amplification but require battery replacement or recharging.

The operational frequency of the RFID system will determine the shape, size, and geometry for the system tag and its antenna. The tags are usually encapsulated to resist environmental affects. The encapsulation materials are normally glass or plastic. This protects the electronics from moisture, shock, corrosion, wear and electrical shorts. The antenna of an RFID system enables a device to convert current and voltage into an electro magnetic signal. Both sides of the equation, interrogator and tag, are required to have an antenna. The transmission frequency will determine whether a magnetic coil antenna, loop, patch, micro strip or an electric dipole design is required.

There is a final step in the RFID system. That is the connection to a host computing system. This system can determine in which mode the interrogator operates. In an environment were tags are passing near the antenna the interrogator can be instructed by the host computing system to always be alert to tags. However, if the antenna of the interrogator were to become portable, the host computer may instruct the reader to energize only at the users command.

The primary market for RFID systems is in any area where optical scanning is used. However, it can also be used where optics would not operate. This includes harsh environments, high speed tracking, identifying hidden items or for long range package scanning.

From a technical point of view, an electromagnetic signal can be effectively generated if the linear dimension of the antenna is comparable with the wavelength of the excitation frequency. In the low to medium frequency bands, the wavelength of the excitation frequency is close to two kilometers. This large length prohibits construction of a true dipole antenna, but a small resonating loop antenna solenoid is effective.

At low to medium RFID frequencies the interrogator and tag are linked through coil antennas. The reader and tag antenna coils are linked using near field magnetic induction coupling between the reader and tag coil antennas. A time varying current passing through the interrogator antenna coil creates a time varying magnetic field in the direction perpendicular to the coil plane. The electro magnetic field is not a propagating wave but rather an attenuating carrier wave.

Passive tags utilize the energy provided by the carrier wave through an induced antenna coil voltage. The voltage is proportional to the product of the number of turns in the tag antenna and the total magnetic flux through the antenna. The integrated circuit within the tag must receive a minimum voltage to become excited and operate. Voltage is built up though an onboard storage capacitor. When sufficient charge has accumulated to reach or surpass the circuit operating voltage, the circuit transistors power up. This produces an electro magnetic signal sent back to the interrogator.

There are two main methods of transmitting data. First there is the full duplex model whereby the tag communicates its data by modulating the carrier wave of the interrogator. This is accomplished by applying a resistive load. A transistor which acts as a load modulator shorts the antenna circuit in sequence to the data. This removes the antenna from resonance at the excitation frequency thereby removing power draw from the interrogator's carrier wave. At the interrogator side of the equation this loading and unloading is read and the data can be reconstructed. Second, in a half duplex RFID system the carrier wave transmits power and then pauses. During the pause period the tag transmits data to the interrogator. It is imperative that both the interrogator and tag use the same transmission method in order to synchronize and successfully exchange data. The specific problem addressed by this Invention is the electro magnetic limiting factor of bodily fluid and bodily tissue which can adversely influence read range and efficiency by detuning an RFID antenna. These fluids include water, bile, fecal matter, and acids.

The bodily tissues include bone, muscle and fat. The problem is that radio waves are absorbed by liquids at ultra high frequencies. The liquid has the effect of absorbing or reflecting the carrier wave. There is the same problem with bodily tissues. The degree of this influence is determined by the operating frequency band used. The absorption or reflection will detune an RFID tag or transponder by shifting its excitation frequency. Interference by liquids and tissue as well as absorption and reflection rates will have the result of decreasing the overall efficacy of the RFID system in question. This Invention contemplates tuning an RFID transponder to each specific fluid or tissue in order to minimize interference. In other words, water, bile, fecal matter and acids as well as bone, muscle and fat would each transmit at different frequencies. Furthermore, by using the chemical structure of the body to power the RFID transponder the detuning effect is ameliorated in that the power of the transponder is dramatically increased. This is because the passive transponder is converted to an active transponder by converting the energy of the body into electro magnetic energy. This energy is stored in an enlarged capacitor of the active transponder for use when required. In spite of the enlarged capacitor the entire system on a chip integrated circuit will be less than the size of a grain of rice.

The fluidic electro magnetic interference is a function of a time varying electro magnetic field which has the effect of causing water and tissue molecules to oscillate from one orientation to another at the frequency of the carrier. This oscillation causes friction. This friction between the molecules converts energy to heat. This peak carrier wave absorption in water and resulting heat generation occurs at microwave frequencies around 2 GHz. The effect of energy absorbed by fluid or tissue denies an RFID tag within the fluid or tissue from its source of power and denies it an information transmission path. This problem can be overcome if the RFID tag is shifted from a passive tag to an active tag. One critical aspect of this fluidic absorption as it applies to this Invention is that lower carrier wave frequencies produce less water absorption. The result is that medium to low frequency RFID systems will outperform a high frequency system in an environment where fluid or tissue is prevalent. It is anticipated by this Invention that the 100 kHz to 300 kHz range be used. This is an unregulated bandwidth.

BACKGROUND OF THE INVENTION

Research by Adam Heller, reported in the Journal of American Chemical Society, disclosed the concept of a functioning grape bio cell. The University of Texas at Austin researcher demonstrated that energy extracted from a grape is enough to power tiny sensors or transmitters. Heller and associates have created a grape bio fuel cell. It produces 2.4 microwatts. As a matter of comparison, it would take several million grapes to power a light bulb. However, 2.4 microwatts is enough power to energize silicon chips. The logical extrapolation from this research is that bio fuel cells could derive power from bodily fluids. As an example, they could power sensors implanted in the body for such purposes as wound monitoring as an adjunct to medical treatment.

Heller is investigating methods of producing electricity within the body through the use of nano technology. One of Heller's papers, "Mechanical and chemical protection of a wired enzyme oxygen cathode by a cubic phase lyotropic liquid crystal," published Feb. 1, 2007 discusses a method of implanting enzymes containing bio fuel electrodes and bio sensors in animals. He demonstrates the use of lyotropic liquid crystal, which, when doped with chemicals, reduces the urate permeation in the liquid crystal. This reduces the physical deterioration of the bio cell.

Heller and colleagues report in the Journal of Chemical Communication during 2003 at pages 518-519 a bio fuel cell. In a paper titled, "A miniature bio fuel cell operating at 0.78 V", they report the highest voltage miniature bio fuel cell. It is a membrane less cell operating at 37 degrees Celsius in pH 5 buffers at 0.78 V.

The work of Heller and colleagues can be distinguished from the present Invention in that it does not contemplate an RFID device powered by a bio cell as implanted into a mammalian body for monitoring purposes. However, his work does establish that the process of converting the energy of the body to electro magnetic energy is a viable operating paradigm.

SUMMARY OF THE INVENTION

This Invention contemplates an ultra low frequency interrogation of RFID transponders when used for counting medical instruments or monitoring medical conditions or when used for tracking mammalian bodies, in general, whether human or animal. The useful, non-obvious and novel step of this Invention is that the RFID transponders are powered by the chemicals in the body. This transforms the RFID transponders from passive to active mode. Furthermore, an additional novel step is that the bodily RFID interrogation is accomplished using ultra low frequency techniques designed to avoid fluidic or tissue interference. Moreover, the antennas on the RFID transponders can be precisely tuned to match the fluidic or tissue environment, whether water, blood, bile, acid or fecal material as well as bone, muscle or fat.

This Invention incorporates by reference Rodgers Application 11676304 titled "RFID interrogation of liquid/metal" and Rodgers Application 11683056 titled "RFID silicon antenna" and Rodgers Application 11686946 titled "Precisely tuned RFID antenna". Application 11676304 is a system to reduce reflection or absorption attenuation during an RFID interrogation conducted in a warehouse or distribution center environment containing items consisting of, or packaged in, metal or liquid. The interrogation is conducted at low frequency to maximize the benefits of the physical properties of low frequency electro magnetic transmissions in relationship to metal or liquid.

The relationship to this Invention is that this Invention contemplates the use of low frequency interrogation to maximize read rates when reading bio cell powered RFID transponders placed into a mammalian body. The low frequency reads obviate the problem of fluidic or tissue detuning of the antenna of the transponder.

Application 11683056 is a system of producing an RFID antenna using the silicon in an integrated circuit as the resonant antenna material for the purpose of reducing the cost of an RFID system and for the purpose of increasing the range and selectivity of the RFID system. According to this Application the base silicon sheets which make up the primary building material of the silicon chip (integrated circuit) is subjected to a laser ablation process. This creates three dimensional nano structures on the surface of the silicon thereby raising its absorption rate of electro magnetic signals. On the reverse side of the same silicon sheet a directional antenna is etched using standard photographic reduction techniques and standard semi conductor industry manufacturing methods. The two sides of the silicon are connected through doping aluminum or copper impurities into these same base silicon sheets causing conductivity within the sheet of silicon.

The relationship to this Invention is that this Invention contemplates the use of silicon antennas as an integrated part of RFID transponders implanted into mammalian bodies in order to minimize the size and costs of an RFID transponder antenna while at the same time maximizing read rates when reading bio cell powered RFID transponders. Application 11686946 is an RFID antenna manufacturing system whereby the RFID antenna becomes an integral part of an integrated circuit package. This RFID manufacturing system includes photo resist manufacturing techniques to produce a template or die specifically designed to mass produce RFID transponders whereby the chip and antenna becomes one integrated unit. The RFID antenna template or die is precisely tuned, using trimming algorithms and laser technology, to resonate with electro magnetic signal increments of 2 megahertz. Accordingly, each increment is assigned to a different category of items being tracked.

The relationship to this Invention is that this Invention contemplates the use of precisely tuned silicon antennas as an integrated part of RFID transponders implanted into mammalian bodies in order to minimize the size and costs of the RFID transponder antenna while at the same time maximizing read rates by precisely tuning to the type of fluidic or tissue interference encountered when reading bio cell powered RFID transponders. In other words, antenna tuned to avoid the specific electro magnetic interference caused by the water, bile, acid or fecal plus bone, muscle and fat tissue which is in the vicinity of the bodily implant and which may cause detuning of the antenna.

PREFERRED EMBODIMENTS

The first embodiment is in the livestock branch of the economy. The Bush administration had plans to give agriculture inspectors the ability to pinpoint the origins of mad cow and other diseases within 48 hours. The idea was that livestock facilities and individual animals would receive identifying numbers, which owners would then use to document the movement of animals using centralized industry databases. Many producers of cattle are expected to use automated systems, such as RFID passive transponders, attached to the ear of cattle to implement this tracking plan. The challenge is that cattle, while appearing to be docile, can be much more skittish than cases or pallets in a warehouse. When thousands of cattle go through a facility, and specifically an RFID gate portal, the cattle do not naturally line up and pass through the RFID interrogators in an orderly fashion. It is common that five or six cattle romp through in a pack. Accordingly, many of the passive devices which need to be read are either not read or misread. Cattle industry analysts now state that only active tags with a broadcast identification range of 300 feet will consistently work for the multiple owners and many environments that cattle pass through from the pasture to the stockyard, feed lots and slaughterhouses. However, active transponders are too expensive and too large to be used effectively in the cattle industry due to the internal battery requirement.

The solution proposed by this Invention is to manufacture an active integrated circuit RFID transponder powered by the enzymes of the cattle and read by low frequency interrogators. According to this embodiment the active integrated circuit would be manufactured of a capsule covered by a porous membrane which would allow the free flow of bodily fluids into and out of the capsule. The enzymes in the bodily fluids of the cattle would produce sufficient electrical charge to power the active transponder. This is through the process of an anode and cathode manufactured into the capsule. The capsule would be of bio compatible silicon. This capsule or casing would be manufactured of material which permits the surrounding tissue to grow up to the casing and bond with it thereby securing the capsule in one position in the body. The antenna would be silicon, as outlined in Application 11683056, and tuned to a low frequency, as outlined in Application 11676304. The capsule would be implanted into the ear of the cattle. The result would be an active transponder which could be interrogated from a far greater distance than currently available. The fluidic and tissue influence of the mammalian body of the cattle would be obviated by the low frequency interrogation. The antenna implant in the ear of the cattle could be tuned to a specific frequency so that the specific bodily fluids or cartilage present in the ear of the cattle would not cause detuning of the antenna. This specific tuning would be as outlined in Application 11686946. Increments of 2 MHz are available according to published research.

The second embodiment is in the field of medicine. One of the challenges faced is the counting of surgical sponges inserted into the human body during an operating room procedure. Cost is the biggest hurdle to tags being implemented in any field that requires item level tracking of low cost products, such as surgical sponges. Furthermore, to overcome the blocking of weak passive radio signals passing in and back out of the body and through bodily fluids and tissues, active tags are required in order to make an RFID embedded sponge operate efficiently. In the current economy an EPC active tag costs between 20 to 40 cents. This price is only available at extraordinarily high volumes. If an active tag could be produced in the less than $0.01 range to be used as an attachment or embedded into operating room sponges the responsibility for counting sponges would shift from the operating room staff to the manufacturer. The result would be decreased insurance costs for hospitals, their staff and doctors. The economic case for using the $0.01 active tag is established. The technical problem is that RFID does not work well with water, blood, and bodily fluids or tissues. This is because radio waves are absorbed by liquids and tissues at ultra high frequencies. This physical fact makes implementation of RFID tags into the bodies full of variably viscous fluids and tissues extremely difficult and pernicious. However, RFID systems can be tuned to obviate the interference of specific bodily fluids such as water, bile, fecal matter, acids and others as well as tissue such as bone, muscle and fat. Furthermore, the power of an active tag obviates the problems of signal collisions and electro magnetic interference caused by bodily fluids. The solution proposed by this Invention is to manufacture an active integrated circuit RFID transponder powered by the enzymes of the human body. The transponder would be read by low frequency interrogators. According to this medical embodiment the active integrated circuit would be manufactured of a capsule covered by a porous membrane which would allow the free flow of bodily fluids into and out of the capsule. The enzymes in the bodily fluids of the patient would produce sufficient electrical charge to power the active transponder. The electro magnetic energy is created by an anode and cathode manufactured into the implantable capsule. The capsule would be of bio compatible silicon. The antenna would be silicon, as outlined in Application 11683056, and tuned to a low frequency, as outlined in Application 11676304. The capsule would be embedded into the sponge. The result would be an active transponder. The fluidic influence of the body of the patient would be obviated by low frequency interrogation. The antenna embedded in the sponge could be tuned to a specific frequency so that the specific bodily fluids or tissue present during specific operating procedure would not cause detuning of the antenna. This specific tuning would be as outlined in Application 11686946. Increments of 2 MHz are available according to published research.

The third embodiment is a corollary to the second. It is in the field of medicine as well. For example there are research and development programs regarding in body antenna chips which are sponsored by the European Union. These programs are designed to assist the aged with reference to medical equipment such as pacemakers, hearing aids and muscle stimulators. These in body chips allow doctors to monitor and adjust pacemakers and hearing aids wirelessly. Furthermore, in body antenna chips with specific sensors attached can monitor the progression of wounds and infections. Designing a device which transmits electro magnetic signals from inside the body poses several difficulties. These include the size of the device, power consumption and the compatibility of materials with the body. Different body tissues, such as muscle, bone, or fat, have a different resistance to electro magnetic signals. Antennas for such devices must be extremely small and efficient to minimize signal loss and preserve power. Pursuant to this embodiment a doctor could monitor the pacemaker of a patient in her office and make adjustments wirelessly. This is as opposed to the current medical environment whereby a problematic pacemaker would have to be surgically removed and an adjusted pacemaker inserted. The solution proposed by this Invention is to manufacture an active integrated circuit RFID transponder powered by the enzymes of the human body. The transponder would be read by low frequency interrogators. According to this medical embodiment the active integrated circuit would be manufactured of a capsule covered by a porous membrane which would allow the free flow of bodily fluids into and out of the capsule. The enzymes in the bodily fluids of the patient would produce sufficient electrical charge to power the active transponder. The electrical charge is generated through an anode and cathode manufactured into the capsule. The capsule would be of bio compatible silicon. The antenna would be silicon, as outlined in Application 11683056, and tuned to a low frequency, as outlined in Application 11676304. The capsule would be embedded into the pacemaker, hearing aid or muscle stimulator. The result would be an active transponder. The disruptive tissue influence of the body of the patient would be obviated by low frequency interrogation. The antenna embedded in the medical device could be tuned to a specific frequency so that the specific bone, muscle, or fat present at the bodily position of the implant would not cause detuning of the miniature silicon antenna integrated into the capsule. This specific tuning is outlined in Application 11686946. Increments of 2 MHz are available according to published research.

The fourth embodiment is in pet tracking. This has in mind the owners of cats and dogs. The pet owner is enabled to locate the pet if it runs astray. The problems and procedure are as above. The one extra wrinkle is that the tracking and locating of the pet could be done remotely. This remote interrogation would be accomplished as outlined in Rodgers Application 11624215 titled "Stolen bicycle (missing chattel) identification, tracking and location; a system and method," which is incorporated herein by reference. In summary, the location of the pet would be determined by triangulation as performed by a cellular telephone network. This is a fee service which could be afforded to cellular telephone network customers.

The fifth Embodiment is for the tracking of criminals. This is a fee service which could be provided by a local cellular telephone network as an adjunct to the work of the Sherriff's department or for FBI purposes. The modus operandi is as above. For example the location of repeat sexual offenders could be monitored at all times. This embodiment is offered as a replacement for the ankle bracelet. This embodiment is equally applicable to prison inmate tracking or sanitarium patient tracking.

All embodiments herein are used as examples only and do not represent limitations to the Claims of this Invention.

I claim:

1. A system and method to manufacture an active RFID integrated circuit as a system on a chip which is powered by enzymes located in mammalian bodies and designed to overcome the antenna detuning effects of fluid and tissue in the mammalian body and whereby said system comprises: providing an RFID Integrated Circuit system on a chip incorporating an antenna constructed of ablated silicon harnessing specific chemical reactions within a mammalian body to produce electrical current or a potential for electrical current; harnessing the electrical current or potential for electrical current within the physical parameters of a system on a chip integrated circuit; shunting the electrical current or potential electrical current via electro magnetic connection to a capacitor whereby said capacitor is an integral part of the system on a chip integrated circuit; storing the electrical current or potential electrical current in the capacitor and whereby the electrical current or potential electrical current powers the system on a chip integrated circuit; manufacturing the system on a chip integrated circuit in part of silicon and in part of a porous membrane which allows the free flow of bodily fluids into and out of the system on a chip integrated circuit; manufacturing an anode and cathode as part of the system on a chip integrated circuit; manufacturing a capsule or casing for that part of the system on a chip integrated chip not made of porous material of material which is coated with a bio material which permits surrounding tissue to grow up to casing and bond to it; tuning the antenna to a specific frequency in order to obviate the detuning effects of whatever mammalian bodily fluids and tissue are present in a given embodiment: providing an RFID interrogator to interrogate the system on a chip interrogated circuit at low frequencies in the 100 kHz to 300 kHz range to neutralize the detuning effects of fluids and tissue in she mammalian body.

2. The system and method of claim 1 whereby a part of the casing or capsule for the system on a chip integrated circuit is constructed of bio compatible glass; or a derivative thereof.

3. The system and method of claim 1 whereby an integral part of the system on a chip integrated circuit is an anode and cathode constructed at a nano scale.

4. The system and method of claim 1 whereby the casing or capsule for the system on a chip integrated circuit is coated with bio conducive material which promotes the bonding of mammalian bodily tissue.

* * * * *